(12) United States Patent
Yamaguchi et al.

(10) Patent No.: US 9,809,750 B2
(45) Date of Patent: Nov. 7, 2017

(54) LIQUID CRYSTAL COMPOSITION

(75) Inventors: Yoko Yamaguchi, Kanagawa (JP); Yuji Yamashita, Ibaraki (JP); Takeshi Hamasaki, Kanagawa (JP)

(73) Assignee: Nanoegg Research Laboratories, Inc., Tokyo (JP)

( * ) Notice: Subject to any disclaimer, the term of this patent is extended or adjusted under 35 U.S.C. 154(b) by 122 days.

(21) Appl. No.: 13/499,344

(22) PCT Filed: Sep. 29, 2010

(86) PCT No.: PCT/JP2010/005863
§ 371 (c)(1), (2), (4) Date: Mar. 30, 2012

(87) PCT Pub. No.: WO2011/040013
PCT Pub. Date: Apr. 7, 2011

(65) Prior Publication Data
US 2012/0196942 A1 Aug. 2, 2012

(30) Foreign Application Priority Data
Sep. 30, 2009 (JP) .................... 2009-226918

(51) Int. Cl.
| | |
|---|---|
| *A61K 8/02* | (2006.01) |
| *C09K 19/54* | (2006.01) |
| *A61K 8/31* | (2006.01) |
| *A61K 8/37* | (2006.01) |
| *A61K 8/891* | (2006.01) |
| *A61K 8/894* | (2006.01) |
| *A61K 9/00* | (2006.01) |
| *A61Q 5/02* | (2006.01) |
| *C09K 19/40* | (2006.01) |
| *C09K 19/52* | (2006.01) |

(52) U.S. Cl.
CPC ............ *C09K 19/54* (2013.01); *A61K 8/0295* (2013.01); *A61K 8/31* (2013.01); *A61K 8/37* (2013.01); *A61K 8/891* (2013.01); *A61K 8/894* (2013.01); *A61K 9/0063* (2013.01); *A61Q 5/02* (2013.01); *C09K 19/406* (2013.01); *C09K 2019/528* (2013.01)

(58) Field of Classification Search
CPC .................................................. A61K 8/0295
See application file for complete search history.

(56) References Cited

U.S. PATENT DOCUMENTS

| | | | |
|---|---|---|---|
| 5,415,875 A * | 5/1995 | Kakoki et al. | 424/581 |
| 8,048,336 B2 | 11/2011 | Tanabe | |
| 2002/0058051 A1* | 5/2002 | Nawaz et al. | 424/401 |
| 2003/0017182 A1 | 1/2003 | Tournilhac | |
| 2007/0065392 A1 | 3/2007 | Simonnet | |
| 2008/0175806 A1 | 7/2008 | Tanabe | |
| 2009/0111963 A1 | 4/2009 | Lafore et al. | |
| 2010/0135938 A1 | 6/2010 | Ishikubo et al. | |

FOREIGN PATENT DOCUMENTS

| | | |
|---|---|---|
| FR | 2816503 A1 | 5/2002 |
| JP | 11-279021 A | 10/1999 |
| JP | 2004-307371 A | 11/2004 |
| JP | 2007-023032 A | 2/2007 |
| JP | 2007-084482 A | 4/2007 |
| JP | 2007-182389 A | 7/2007 |
| JP | 2008-174634 A | 7/2008 |
| JP | 2008-195924 A | 8/2008 |
| JP | 2008-291027 A | 12/2008 |
| JP | 2009-504876 A | 2/2009 |
| JP | 2009-191017 A | 8/2009 |

OTHER PUBLICATIONS

English Translation of the Office Action issued for the Brazilian corresponding application No. BR112012007350-8, Mar. 29, 2017.

* cited by examiner

*Primary Examiner* — Johann R Richter
*Assistant Examiner* — Danielle Sullivan
(74) *Attorney, Agent, or Firm* — Brundidge & Stanger, P.C.

(57) ABSTRACT

A liquid crystal composition contains liquid crystals containing one kind of or two or more kinds of silicone surfactants, a phenyl-modified silicone oil and water. The liquid crystal composition of the present invention contains 5 to 95% by weight in total of one kind of or two or more kinds of silicone surfactants, 0.1 to 90% by weight of a phenyl-modified silicone oil and 0.1 to 90% by weight of water. The liquid crystal composition of the present invention can solubilize hydrophobic compounds having poor solubility (for example, hydrocarbon oils such as squalane, fatty acids such as oleic acid and lipoic acid and ester oils such as cetyl isooctanoate) and is thus useful, for example, as toiletry materials and cosmetic materials.

9 Claims, 12 Drawing Sheets

LIQUID CRYSTAL COMPOSITION

TECHNICAL FIELD

The present invention relates to a novel liquid crystal composition containing silicone compounds.

BACKGROUND ART

Silicone is a compound which is not only colorless and odorless but has extremely low bioactivity. The addition of silicone compound to a composition for skin applications can realize remarkable improvement in properties such as improvement in lubriciousness, impartment of water repellency and gloss, and improvement in a refreshed feel.

Conventionally, emulsions have been known as silicone compositions for skin applications (see Patent Literature 1 and 2).

Patent Literature 1 describes a large internal aqueous phase water-in-oil type (W/O type) emulsion cosmetic composition containing cross-linked polyether-modified silicone(s), a carboxymethyl cellulose salt, water and a low viscosity silicone oil. The cosmetics of Patent Literature 1 uses a paste-like polyether-modified silicone composition containing cross-linked polyether-modified silicone(s) and a low viscosity silicone oil as an oil phase and an aqueous solution of a carboxymethyl cellulose salt as an aqueous phase, thereby providing both feeling of water running over at use and stability during transportation.

Patent Literature 2 describes a sunscreen water-in-oil type (W/O type) emulsion cosmetic composition containing 4-(1, 1-dimethylethyl)-4'-methoxydibenzoylmethane, benzotriazole derivative(s), a silicone oil, a silicone surfactant and water. The sunscreen cosmetics of Patent Literature 2 realizes superior ultraviolet absorption properties in the UV-A region while reducing the staining tendency on clothing.

Moreover, in recent years, there have been disclosed silicone liquid crystal compositions (for example, see Patent Literature 3). Patent Literature 3 describes a method for preparing a silicone liquid crystal from a ≡Si—H containing polysiloxane with polyether groups, a α,ω-dienes and water. It is also described that the silicone liquid crystals prepared by this method can be used for a variety of applications including use as delivery vehicles for active ingredients in pharmaceutical and cosmetic applications.

CITATION LIST

Patent Literature

PTL 1 Japanese Patent Application Laid-Open (Kokai) No. 2004-307371
PTL 2 Japanese Patent Application Laid-Open (Kokai) No. 2007-182389
PTL 3 Japanese Patent Application Laid-Open (Kohyo) No. 2009-504876

SUMMARY OF INVENTION

Technical Problem

An object of the present invention is to provide a novel liquid crystal composition containing silicone compounds.

Solution to Problem

The present inventors have found that, in the course of investigating a novel liquid crystal composition containing silicone compounds, a liquid crystal composition can be prepared from silicone surfactant(s) and water by using one specific kind of silicone surfactants, or by using two or more kinds of specific silicone surfactants in combination.

Then, the present inventors have found that, in the course of investigating the suitability and usability of this liquid crystal composition for various materials, hydrophobic compounds having poor solubility in water (such as, for example, hydrocarbon oils, fatty acids and ester oils compounded in cosmetics and the like) can be solubilized in the inner domains of liquid crystals by further compounding a phenyl-modified silicone oil as a component of the liquid crystal composition.

The present invention is based on the aforementioned findings and has the following characteristics.

[1] A liquid crystal composition containing one kind of or two or more kinds of silicone surfactants, a phenyl-modified silicone oil and water.

[2] The liquid crystal composition according to [1], containing 5 to 95% by weight in total of the one kind of or two or more kinds of silicone surfactants, 0.1 to 90% by weight of the phenyl-modified silicone oil and 0.1 to 90% by weight of the water.

[3] The liquid crystal composition according to [1] or [2], wherein the two or more kinds of silicone surfactants are a combination of two or more kinds of pendant-type silicone surfactants.

[4] The liquid crystal composition according to any one of [1] to [3], wherein the phenyl-modified silicone oil is a monophenyl silicone oil.

[5] The liquid crystal composition according to any one of [1] to [4], further containing a hydrocarbon oil, a fatty acid, an ester oil or a combination thereof.

[6] The liquid crystal composition according to [5], wherein the hydrocarbon oil is squalane.

[7] The liquid crystal composition according to [5], wherein the ester oil is cetyl isooctanoate.

[8] The liquid crystal composition according to any one of [1] to [7], which has been compounded in cosmetics.

[9] A skin external composition containing the liquid crystal composition according to any one of [1] to [7].

[10] A skin or hair cleaning agent containing the liquid crystal composition according to any one of [1] to [7].

Advantageous Effects of Invention

The present invention makes it possible to provide a novel liquid crystal composition containing silicone compounds. The liquid crystal composition of the present invention can solubilize hydrophobic compounds having poor solubility in water (for example, squalane), and is thus useful, for example, as cosmetic materials.

DETAILED DESCRIPTION OF PREFERRED EMBODIMENTS

Figure 1A:
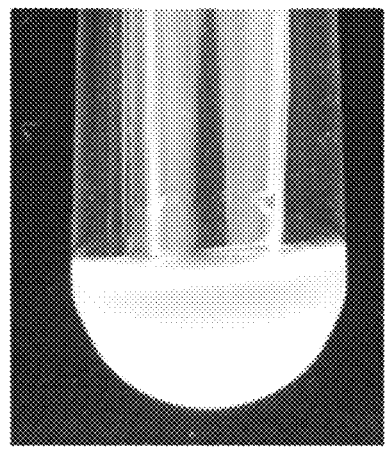
FIG. 1A is a photograph showing a mixture of two kinds of silicone surfactants.

A liquid crystal composition of the present invention will now be described. As used herein, the term "silicone compound" means any compound having siloxane bonds Si—O (also referred to as "polysiloxane").

The liquid crystal composition of the present invention contains liquid crystals containing one kind of or two or more kinds of silicone surfactants, a phenyl-modified silicone oil and water. The liquid crystal composition of the present invention preferably contains no component other than the aforementioned liquid crystal, however, may contain several percentages (for example, 10% or less, preferably 5% or less, more preferably 3% or less and most preferably 1% or less) of components/structures (such as, for example, vesicles, L3 and sejunction water) other than the liquid crystal.

The kind of the liquid crystal contained in the liquid crystal composition of the present invention is not particularly limited as long as the liquid crystal has an ordered structure. Examples of such a liquid crystal include lamellar liquid crystals, cubic liquid crystals, hexagonal liquid crystals and reverse hexagonal liquid crystals. Examples of cubic liquid crystals include discontinuous cubic liquid crystals, inverted-type discontinuous cubic liquid crystals, bicontinuous cubic liquid crystals and inverted-type bicontinuous cubic liquid crystals. Through observation by a polarizing microscope, the liquid crystal composition of the present invention can be confirmed to contain liquid crystals. Also, the liquid crystal structure can be confirmed by Small Angle X-ray Scattering (SAXS).

The liquid crystal composition of the present invention contains silicone surfactant(s). The use of silicone surfactant(s) can improve the usability when applied on skin. In addition, the use of silicone surfactant(s) can increase the amount of a phenyl-modified silicone oil to be compounded, compared with that in the case of using other surfactants (see Examples). As described below, increase in the amount of a phenyl-modified silicone oil to be compounded can increase the amount of other oils to be compounded such as hydrocarbon oils, fatty acids and ester oils.

A "silicone surfactant" means a nonionic surfactant having dimethyl polysiloxane as a hydrophobic group and polyoxyalkylene mono-glycol ether (polyether) as a hydrophilic group. The structure of the silicone surfactant is not particularly limited. For example, the silicone surfactant may be a pendant-type silicone surfactant and may be an AB-type silicone surfactant. A "pendant-type silicone surfactant" means a graft copolymer having polyether (side chain) linked to dimethyl polysiloxane (main chain). Also, an "AB-type silicone surfactant" means a block copolymer having dimethyl polysiloxane and polyether linked in a linear fashion. Examples of the silicone surfactant include dimethylpolysiloxane polyethylene glycol and dimethylpolysiloxane (polyoxyethylene-polyoxypropylene) copolymer.

The silicone surfactant contained in the liquid crystal composition of the present invention may be one kind or a combination of two or more kinds.

When using one kind of silicone surfactant, the silicone surfactant preferably has a HLB value in the range from 4.0 to 10.0 and a viscosity of 400 mm$^2$/s or more. Stable crystals can be easily formed by using the silicone surfactant having a HLB value and viscosity in this range (see Examples). The upper limit of the viscosity of the silicone surfactant is not particularly limited, but is 20,000 mm$^2$/s for example.

When using two or more kinds of silicone surfactants, a combination of the silicone surfactants is not particularly limited. However, it is preferred that at least one kind of silicone surfactant to be used has a low HLB value. When HLB values of all silicone surfactants are high, the formation of stable liquid crystals can be interfered. A "high HLB value" herein means that a HLB value is 13 or more. Further, a pendant-type silicone surfactant is preferably combined with a pendant-type silicone surfactant. Similarly, an AB-type silicone surfactant is preferably combined with an AB-type silicone surfactant. When silicone surfactants different in structure are combined, the formation of stable liquid crystals can be interfered. In the view point of forming stable liquid crystals, a combination of pendant-type silicone surfactants is more preferable than a combination of AB-type silicone surfactants (see Examples).

The concentration of the silicone surfactant(s) in the liquid crystal composition of the present invention is preferably in the range from 5 to 95% by weight, more preferably in the range from 25 to 95% by weight, still more preferably in the range from 50 to 95% by weight, as the sum of the concentrations of all the silicone surfactants. When the concentration of the silicone surfactant(s) is less than 5% by weight or more than 95% by weight, it is difficult to form liquid crystals due to the occurrence of phase separation or emulsification. Moreover, the higher concentration of the silicone surfactant(s) (25% by weight or higher, preferably 50% by weight or higher) enhances the ability of the liquid crystal composition of the present invention to solubilize oil (such as, for example, hydrocarbon oils, fatty acids and ester oils).

A silicone oil contained in the liquid crystal composition of the present invention is preferably a phenyl-modified silicone oil. The use of a phenyl-modified silicone oil can enhance the ability of the liquid crystal composition of the present invention to solubilize oil (see Examples). Examples of the phenyl-modified silicone oil include methylphenyl polysiloxane, diphenyl polysiloxane and the like. In the view point of enhancing the ability of the liquid crystal composition of the present invention to solubilize oil, a monophenyl-modified silicone oil is more preferable than a biphenyl-modified silicone oil as the phenyl-modified silicone oil (see Examples).

The concentration of the phenyl-modified silicone oil in the liquid crystal composition of the present invention is preferably in the range from 0.1 to 90% by weight. When the concentration of the phenyl-modified silicone oil is less than 0.1% by weight, the ability of the liquid crystal composition of the present invention to solubilize oil cannot be enhanced sufficiently. On the other hand, when the concentration of the phenyl-modified silicone oil exceeds 90% by weight, it becomes difficult to form liquid crystals.

Water contained in the liquid crystal composition of the present invention is, for example, pure water, distilled water and the like. The concentration of water in the liquid crystal composition of the present invention is preferably in the range from 0.1 to 90% by weight. When the concentration of water is less than 0.1% by weight or exceeds 90% by weight, it becomes difficult to form liquid crystals.

In addition, the liquid crystal composition of the present invention may contain a polyhydric alcohol. The use of a polyhydric alcohol can facilitate to form stable liquid crystals. Examples of the polyhydric alcohol include polyalkylene glycols such as polyethylene glycol, glycerin, propylene glycol, 1,3-propanediol, 2-butene-1,4-diol, pentane-1,5-diol, 2,2-dimethylpropane-1,3-diol, 3-methylpentane-1,5-diol, pentane-1,2-diol, 2,2,4-trimethylpentane-1,3-diol, 2-methylpropane-1,3-diol, hexylene glycol, 1,3-butylene glycol, dipropylene glycol, diethylene glycol and triethylene glycol. The polyhydric alcohol may be one kind or a combination of two or more kinds. The concentration of the polyhydric alcohol in the liquid crystal composition of the present invention is preferably in the range from 1 to 55% by weight, more preferably in the range from 3 to 52% by weight, still more preferably in the range from 5 to 50% by weight.

In addition, the liquid crystal composition of the present invention may contain cholesterol as a cosurfactant. The use of a cosurfactant can facilitate to form stable liquid crystals. The concentration of the cosurfactant in the liquid crystal composition of the present invention is preferably in the range from 0.01 to 10% by weight.

In addition to the aforementioned essential components (silicone surfactant(s), a phenyl-modified silicone oil and water), the liquid crystal composition of the present invention may contain commonly used aqueous components and oil components in such a range that the advantages of the present invention are not impaired. Examples of the additional components include moisturizing agents, antiseptic agents, antioxidants, ultraviolet absorbers, cosmetic components, vitamins, flavors, aroma retention agents, thickeners, color pigments, photoluminescent agents, organic powders, metal oxides, tar dyes and the like.

The liquid crystal composition of the present invention can be prepared by mixing silicone surfactant(s), a phenyl-modified silicone oil and water which are to be components thereof at a predetermined temperature and ratio. The mixing ratio of the silicone surfactant(s), a phenyl-modified silicone oil and water varies depending on the kind of the silicone surfactant(s) and phenyl-modified silicone oil used. Those skilled in the art can appropriately select the mixing ratio so that the mixture can exhibit a liquid crystalline phase, preferably a single liquid crystalline phase. Incidentally, the components may temporarily be heated before or after mixing when needed.

The liquid crystal composition of the present invention can enhance the solubility of substances having poor solubility in water by incorporating the substances in the liquid crystal structure. In addition, the liquid crystal composition of the present invention can incorporate a large amount of organic oil such as hydrocarbon oils (for example, squalane), fatty acids or ester oils (for example, cetyl isooctanoate) in the liquid crystal structure. Therefore, the liquid crystal composition of the present invention can be applicable to, for example, a skin external composition and a skin or hair cleaning agent. For example, the liquid crystal composition of the present invention can be compounded in cosmetics. More specifically, the liquid crystal composition of the present invention can be applicable to cosmetic lotions, creams, milky lotions, cleansing agents, face washes, body cleaning agents, hair cleaning agents, hair tonics, hair nutritional supplements (hair treatment agents), hair coloring agents, hair coating agents (hair manicures), deodorants, depilatories, make-up items (such as lip sticks, eye shadows, eye liners, mascaras) and the like.

The present invention will now be described in detail with reference to examples, but the invention is not restricted to the following examples.

EXAMPLES

Example 1

The present example shows an example which prepared the liquid crystal composition of the present invention by using two kinds of silicone surfactants, a phenyl-modified silicone oil and water.

As silicone surfactants, SS-2804 (polyether-modified silicone (pendant-type), main component: PEG-12 dimethicone, HLB: 13.0, Dow Corning Toray Co., Ltd.) and SS-2910 (polyether-modified silicone (pendant-type), main component: PEG-10 dimethicone, HLB: 4.0, Dow Corning Toray Co., Ltd.) were prepared. Also, as a phenyl-modified silicone oil, SH556 (phenyl trimethicone (content: 60% by weight or more), Dow Corning Toray Co., Ltd.) was prepared.

Figure 1B:
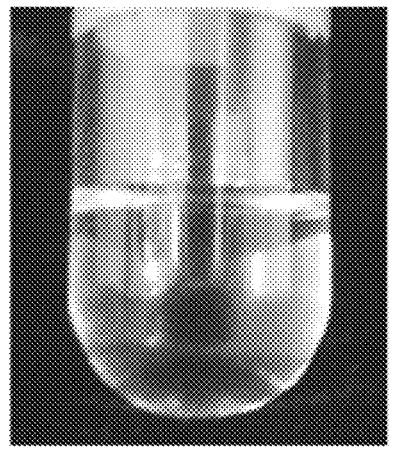
FIG. 1B is a photograph showing a liquid crystal composition containing two kinds of silicone surfactants and pure water.

SS-2804 (0.8 g), SS-2910 (0.8 g) and pure water (0.4 g) were mixed until the mixture becomes uniform, thereby preparing a transparent liquid crystal composition (80% by weight mixed surfactant aqueous solution). FIG. 1A is a photograph showing the mixture of two kinds of silicone surfactants. FIG. 1B is a photograph showing the liquid crystal composition containing two kinds of silicone surfactants and pure water.

Figure 2C:
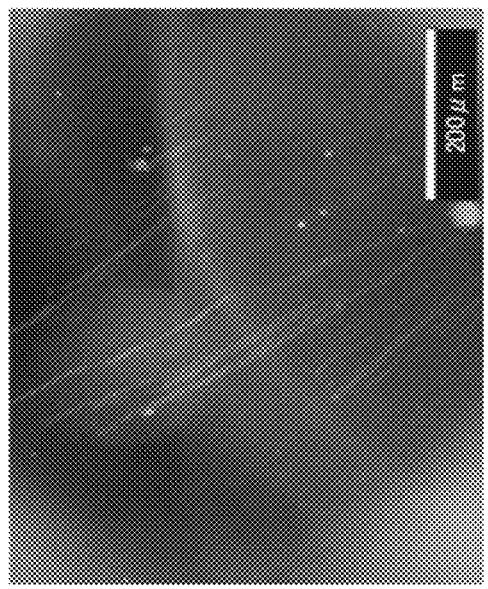
FIGS. 2B and 2C are polarizing micrographs of a liquid crystal composition containing two kinds of silicone surfactants and pure water.
Figure 2B:
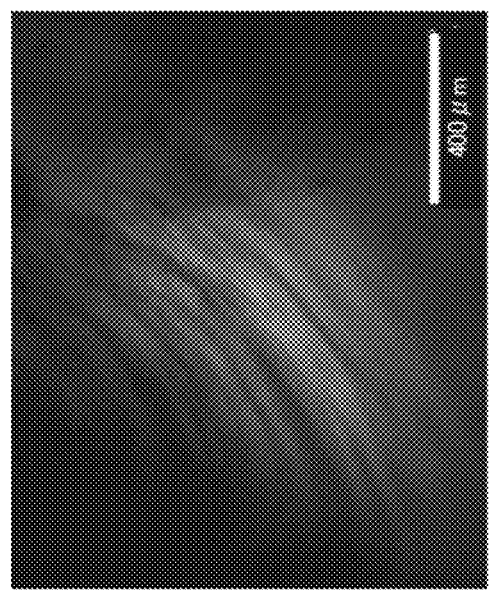
Figure 2A:
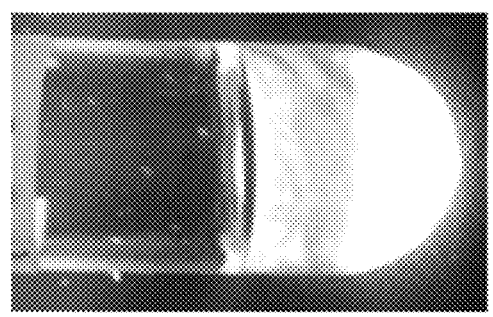
FIG. 2A is a photograph showing a liquid crystal composition containing two kinds of silicone surfactants and pure water observed through a polarizing plate.

FIG. 2A is a photograph showing the liquid crystal composition containing two kinds of silicone surfactants and pure water observed through a polarizing plate. FIGS. 2B and 2C are polarizing micrographs of the liquid crystal composition containing two kinds of silicone surfactants and pure water. As shown in these photographs, a texture can be seen by observing the liquid crystal composition containing two kinds of silicone surfactants and pure water through a polarizing plate, which indicates that a liquid crystal structure exists in this liquid crystal composition.

Figure 3:
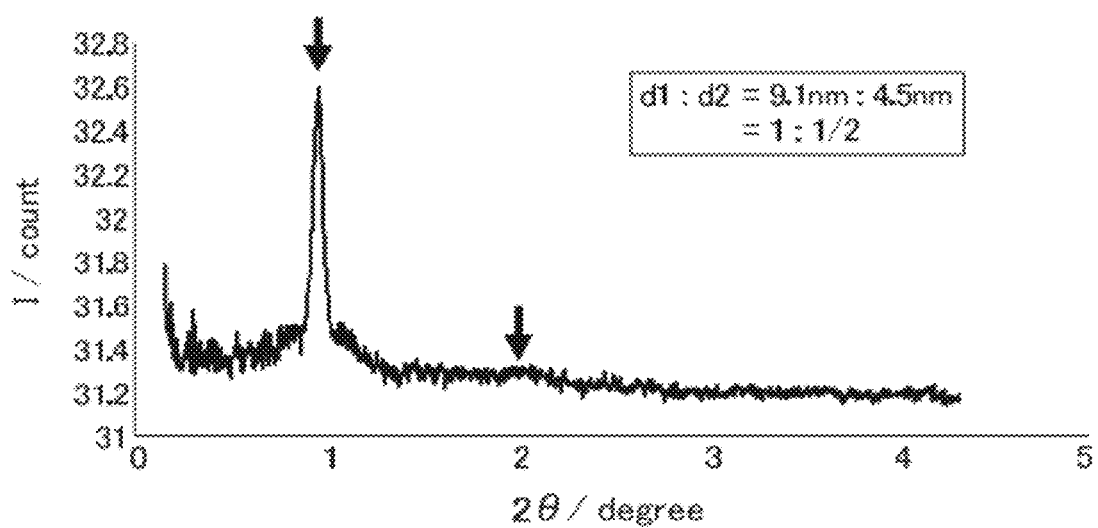
FIG. 3 is a graph showing the result of an SAXS analysis of a liquid crystal composition containing two kinds of silicone surfactants and pure water.

FIG. 3 is a graph showing the result of an SAXS analysis of the liquid crystal composition containing two kinds of silicone surfactants and pure water. As shown in this graph, the ratio of interlayer spacings (d1:d2) calculated from the first peak and the second peak is 1:1/2, which indicates that the liquid crystal structure existing in this liquid crystal composition is a lamellar (Lα) liquid crystal structure.

Figure 4:
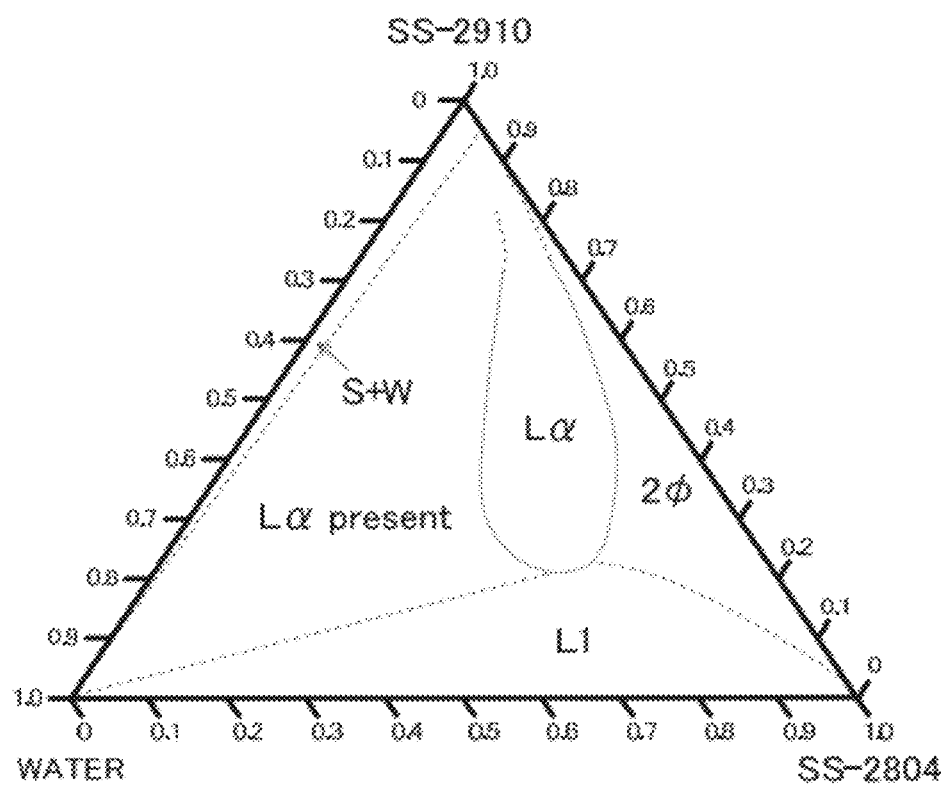
FIG. 4 is an equilibrium phase diagram of a composition containing SS-2804, SS-2910 and water at room temperature.

FIG. 4 is an equilibrium phase diagram of a composition containing SS-2804, SS-2910 and water at room temperature. "Lα" means lamellar liquid crystals, "Lα present" means an existing region of lamellar liquid crystals, "S" means a solid phase, "W" means water, "2φ" means a two-phase region and "L1" means a micellar aqueous solution or monodispersed solution. This drawing also indicates that the aforementioned liquid crystal composition is composed of lamellar liquid crystals.

Figure 5:
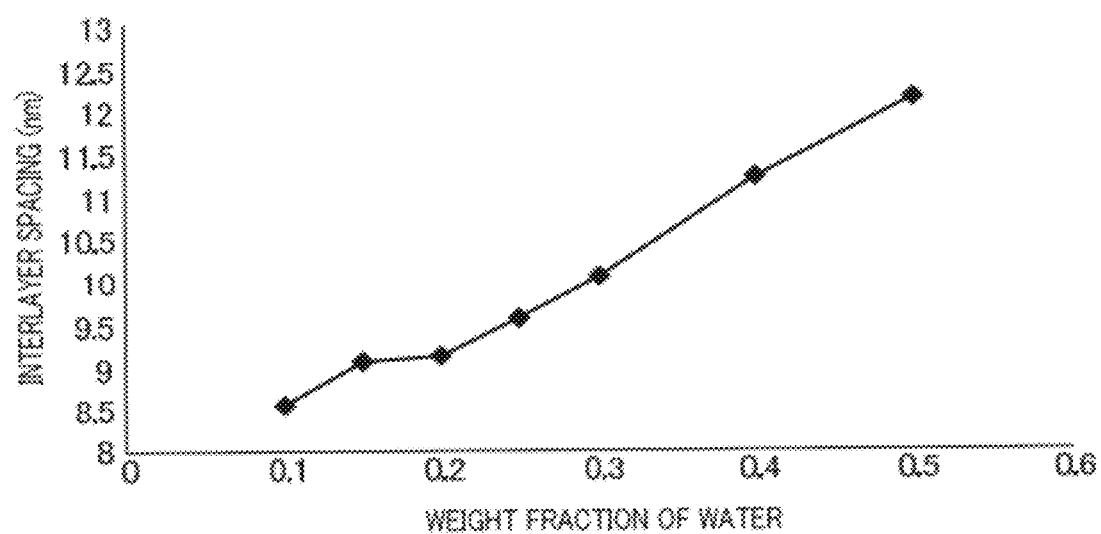
FIG. 5 is a graph showing the relationship between the concentration of water and the interlayer spacing of lamellar liquid crystals, when changing the amount of pure water in a liquid crystal composition containing two kinds of silicone surfactants and pure water.

FIG. 5 is a graph showing the relationship between the concentration of water and the interlayer spacing of lamellar liquid crystals, when changing the amount of pure water of the liquid crystal composition containing two kinds of silicone surfactants and pure water. As the weight fraction of water increases, the interlayer spacing of lamellar liquid crystals increases, which indicates that this liquid crystal composition can include at least 50% of water by weight between lamellar layers.

Then, SH556 (phenyl-modified silicone oil) was added to this liquid crystal composition to prepare the liquid crystal composition of the present invention. Moreover, as comparative examples, squalane (comparative example; organic oil) or SH200C20CS (comparative example; non-modified silicone oil; polydimethyl siloxane (content: 99% by weight or more), Dow Corning Toray Co., Ltd.) was added instead of SH556, thereby preparing liquid crystal compositions of comparative examples.

The solubilized concentration of oil (SH556, squalane or SH200C20CS) in each liquid crystal composition was evaluated. The solubilized concentration (saturated concentration of solubilization) of oil was measured by sample appearance, for example, cloudiness or phase separation.

Figure 6:
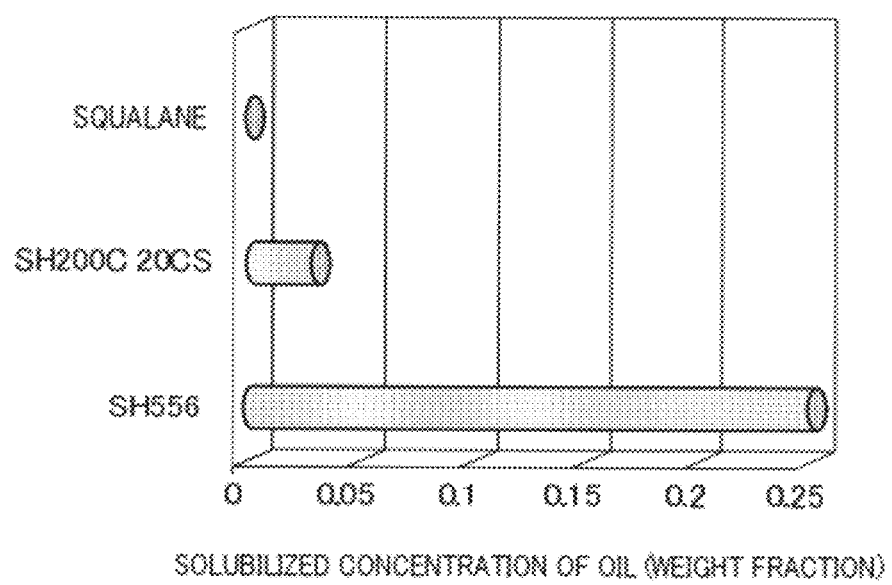
FIG. 6 is a graph showing the solubilized concentration of oil when the oil was added to liquid crystal compositions containing two kinds of silicone surfactants and pure water.

FIG. 6 is a graph showing the solubility concentration of oil (SH556, squalane or SH200C20CS) when the oil was added to the liquid crystal composition containing two kinds of silicone surfactants and pure water. As shown in this graph, SH556 could be dissolved in the liquid crystal composition at at least 25% by weight and SH200C20CS could be dissolved in the liquid crystal composition at 3% by weight. On the other hand, squalane could not be dissolved in the liquid crystal composition. This graph shows that the liquid crystal composition containing silicone surfactants has high compatibility to a silicone oil (in particular, a phenyl-modified silicone oil).

Then, SH200C20CS or squalane was added to the liquid crystal composition of the present invention (containing 3 to 20% by weight of SH556) and the solubilized concentration of oil (SH200C20CS or squalane) was determined. As a result, the liquid crystal composition of the present invention containing 20% by weight of SH556 could contain SH200C20CS up to 20% by weight. In addition, the liquid crystal composition of the present invention containing 3.125% by weight of SH556 could contain squalane up to 3.125% by weight. These results show that the liquid crystal composition of the present invention containing a phenyl-modified silicone oil can dissolve more oil such as non-modified silicone oils or organic oils, as compared with liquid crystal compositions containing no phenyl-modified silicone oil.

As described above, the liquid crystal composition of the present invention can be used for a skin external composition and a skin or hair cleaning agent due to high solubility of organic oils and silicone oils.

Example 2

The present example shows an example which prepared the liquid crystal composition of the present invention by compounding a monophenyl silicone oil or biphenyl silicone oil as a phenyl-modified silicone oil.

As silicone surfactants, the aforementioned SS-2804 and SS-2910 were prepared. Also, as a phenyl-modified silicone oil, KF50-100CS (biphenyl silicone oil; Shin-Etsu Chemical Co., Ltd.) was further prepared in addition to the aforementioned SH556 (monophenyl silicone oil).

In the same procedure as in Example 1, SS-2804, SS-2910 and pure water were mixed until the mixture becomes uniform, thereby preparing an 80% by weight mixed surfactant aqueous solution (transparent liquid crystal composition). Then, a mixed oil of SH556 and squalane or a mixed oil of KF50-100CS and squalane was added to the mixed surfactant aqueous solution, thereby preparing the liquid crystal compositions of the present invention. The weight ratio of a phenyl-modified silicone oil (SH556 or KF50-100CS) and squalane is 1:1 in each mixed oil. Moreover, as a comparative example, squalane alone was added to the mixed surfactant aqueous solution to prepare a liquid crystal composition for the comparative example.

The solubilized concentration of oil (mixed oil or squalane) in each liquid crystal composition was evaluated. The solubilized concentration (saturated concentration of solubilization) of oil was measured by sample appearance, for example, cloudiness or phase separation.

Figure 7:
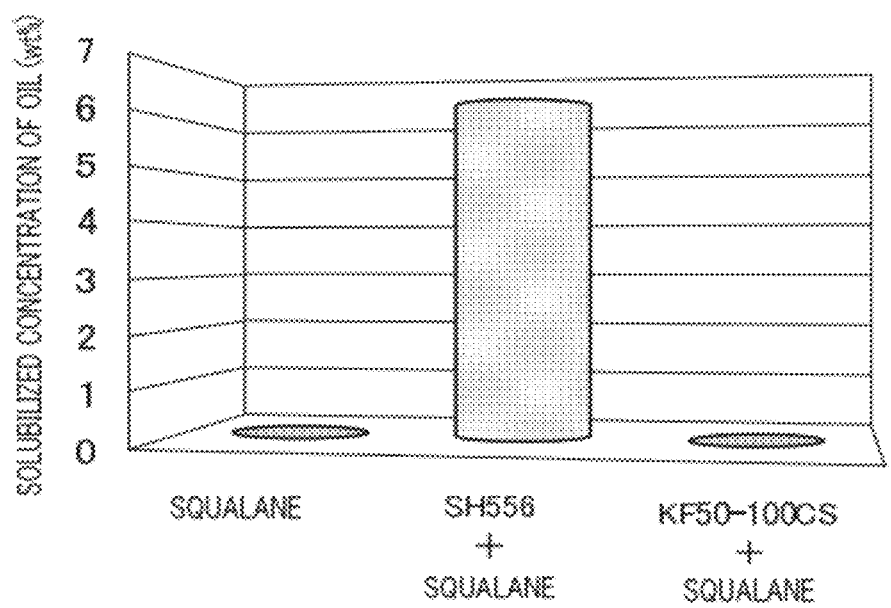
FIG. 7 is a graph showing the solubilized concentration of oil containing a monophenyl silicone oil or biphenyl silicone oil when the oil was added to a mixed surfactant aqueous solution.

FIG. 7 is a graph showing the solubilized concentration of oil (mixed oil or squalane) when the oil was added to the mixed surfactant aqueous solution. As shown in FIG. 7, SH556 showed the effect of enhancing solubility of squalane. However, KF50-100CS did not show such an effect. This may be because the molecular weight of KF50-100CS (viscosity: 100 mm$^2$/s) is larger than that of SH556 (viscosity: 22 mm$^2$/s).

The results described above show that a monophenyl silicone oil is more preferable compared with a biphenyl silicone oil in terms of the ability to solubilize hydrocarbon oils such as squalane.

Example 3

The present example shows an example which prepared the liquid crystal composition of the present invention by compounding pendant-type silicone surfactants or AB-type silicone surfactants as silicone surfactants.

As pendant-type silicone surfactants, the aforementioned SS-2804 and SS-2910 were prepared. Also, as AB-type silicone surfactants, FZ-2222 (polyether-modified silicone (AB-type), HLB: 6.0, Dow Corning Toray Co., Ltd.) and FZ-2233 (polyether-modified silicone (AB-type), HLB: 2.5, Dow Corning Toray Co., Ltd.) were prepared. As a phenyl-modified silicone oil, the aforementioned SH556 was prepared.

In the same procedure as in Example 1, SS-2804, SS-2910 and pure water were mixed until the mixture becomes uniform, thereby preparing an 80% by weight mixed surfactant aqueous solution. In the same manner, FZ-2222, FZ-2233 and pure water were mixed until the mixture becomes uniform, thereby preparing an 80% by weight mixed surfactant aqueous solution. The weight ratio of two kinds of surfactants is 1:1 in each mixed surfactant aqueous solution. Then, SH556 was added to each mixed surfactant aqueous solution to prepare the liquid crystal compositions of the present invention.

The solubilized concentration of SH556 in each liquid crystal composition was evaluated. The solubilized concentration (saturated concentration of solubilization) of SH556 was measured by sample appearance, for example, cloudiness or phase separation.

Figure 8:
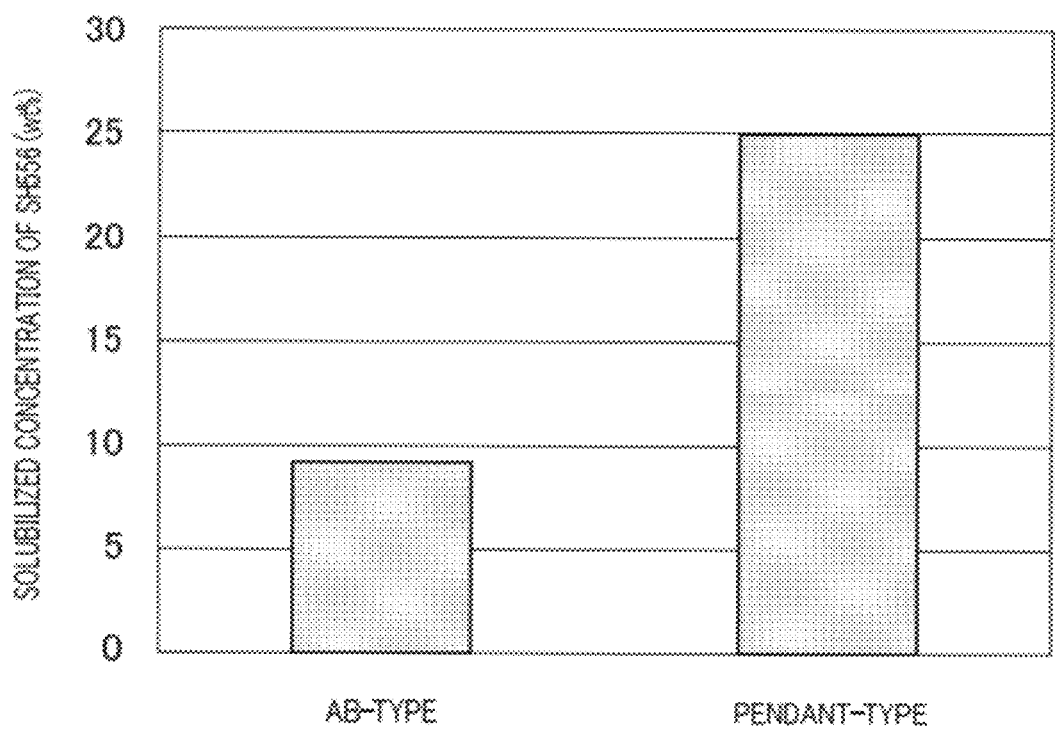
FIG. 8 is a graph showing the solubilized concentration of SH556 when SH556 was added to mixed surfactant aqueous solutions containing pendant-type silicone surfactants or AB-type silicone surfactants.

FIG. 8 is a graph showing the solubilized concentration of SH556 when SH556 was added to the mixed surfactant aqueous solutions. As shown in FIG. 8, the liquid crystal composition containing pendant-type silicone surfactants (SS-2804/SS-2910 aqueous solution) has higher ability to solubilize SH556 compared with the liquid crystal composition containing AB-type silicone surfactants (FZ-2222/FZ-2233 aqueous solution).

The results described above show that pendant-type silicone surfactants are more preferable compared with AB-type silicone surfactants in terms of the ability to solubilize a phenyl-modified silicone oil.

Example 4

The present example shows an example which prepared the liquid crystal composition of the present invention by compounding two kinds of pendant-type silicone surfactants as silicone surfactants.

Silicone surfactants shown in Table 1 below (all of which are polyether-modified silicone (pendant-type), Dow Corning Toray Co., Ltd.) were prepared. Also, as a phenyl-modified silicone oil, the aforementioned SH556 (monophenyl silicone oil) was prepared.

TABLE 1

| Product name | Main component | HLB value | Viscosity (mm$^2$/s) |
|---|---|---|---|
| SH3771M | PEG-12dimethicone | 13.0 | 400 |
| SH3772M | PEG-12dimethicone | 6.0 | 1050 |
| SH3773M | PEG-12dimethicone | 8.0 | 650 |
| SH3775M | PEG-12dimethicone | 5.0 | 1600 |
| SS2802 | PEG-10dimethicone | 13.0 | 130 |
| SS2804 | PEG-12dimethicone | 13.0 | 390 |
| SS2910 | PEG-10dimethicone | 4.0 | 550 |

In the same procedure as in Example 1, two kinds of surfactants (the first surfactant and the second surfactant) and pure water were mixed until the mixture becomes uniform, thereby preparing an 80% by weight mixed surfactant aqueous solution. The weight ratio of the first surfactant and the second surfactant is 1:1. Table 2 shows combinations of two kinds of surfactants.

TABLE 2

| Classification | First surfactant | Second surfactant |
|---|---|---|
| A | SS2804 | SS2910 |
| B | SH3771M | SH3773M |
| C | SH3772M | SH3775M |
| D | SH3773M | SS2910 |
| E | SH3775M | SS2804 |
| F | SS2802 | SS2910 |

Then, a mixed oil of SH556 and squalane was added to each mixed surfactant aqueous solution, thereby preparing the liquid crystal compositions of the present invention. The weight ratio of SH556 and squalane is 1:1 in the mixed oil. Moreover, as comparative examples, squalane alone was added to the mixed surfactant aqueous solutions to prepare liquid crystal compositions for the comparative examples.

The solubilized concentration of oil (a mixed oil of SH556 and squalane or squalane) in each liquid crystal composition was evaluated. The solubilized concentration (saturated concentration of solubilization) of oil was measured by sample appearance, for example, cloudiness or phase separation.

Figure 9:
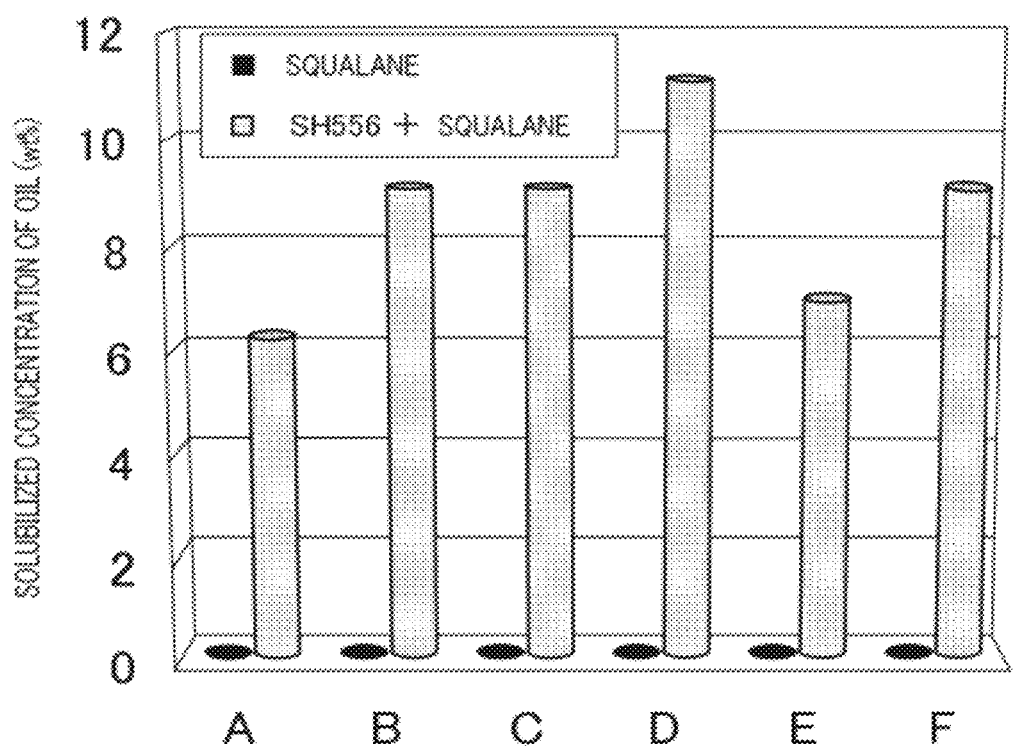
FIG. 9 is a graph showing the solubilized concentration of oil when the oil was added to mixed surfactant aqueous solutions containing two kinds of pendant-type silicone surfactants.

FIG. 9 is a graph showing the solubilized concentration of oil (a mixed oil of SH556 and squalane or squalane) when the oil was added to the mixed surfactant aqueous solutions. As shown in FIG. 9, SH556 showed the effect of enhancing solubility of squalane in all liquid crystal compositions prepared by using any mixed surfactant aqueous solution.

Example 5

The present example shows that the liquid crystal compositions of the present invention can solubilize fatty acids.

As silicone surfactants, the aforementioned SS-2804 and SS-2910 were prepared. Also, as a phenyl-modified silicone oil, the aforementioned SH556 (monophenyl silicone oil) was prepared.

In the same procedure as in Example 1, SS-2804, SS-2910 and pure water were mixed until the mixture becomes uniform, thereby preparing an 80% by weight mixed surfactant aqueous solution (transparent liquid crystal composition). Then, a mixed oil of SH556 and α-lipoic acid or a mixed oil of SH556 and oleic acid was added to the mixed surfactant aqueous solution, thereby preparing the liquid crystal compositions of the present invention. The weight ratio of SH556 and a fatty acid (α-lipoic acid or oleic acid) is 1:1 in each mixed oil. Moreover, as comparative examples, α-lipoic acid alone or oleic acid alone was added to the mixed surfactant aqueous solution to prepare liquid crystal compositions for the comparative examples.

The solubilized concentration of oil (a mixed oil of SH556 and α-lipoic acid, a mixed oil of SH556 and oleic acid, α-lipoic acid or oleic acid) in each liquid composition was evaluated. The solubilized concentration (saturated concentration of solubilization) of oil was measured by sample appearance, for example, cloudiness or phase separation.

Figure 10:
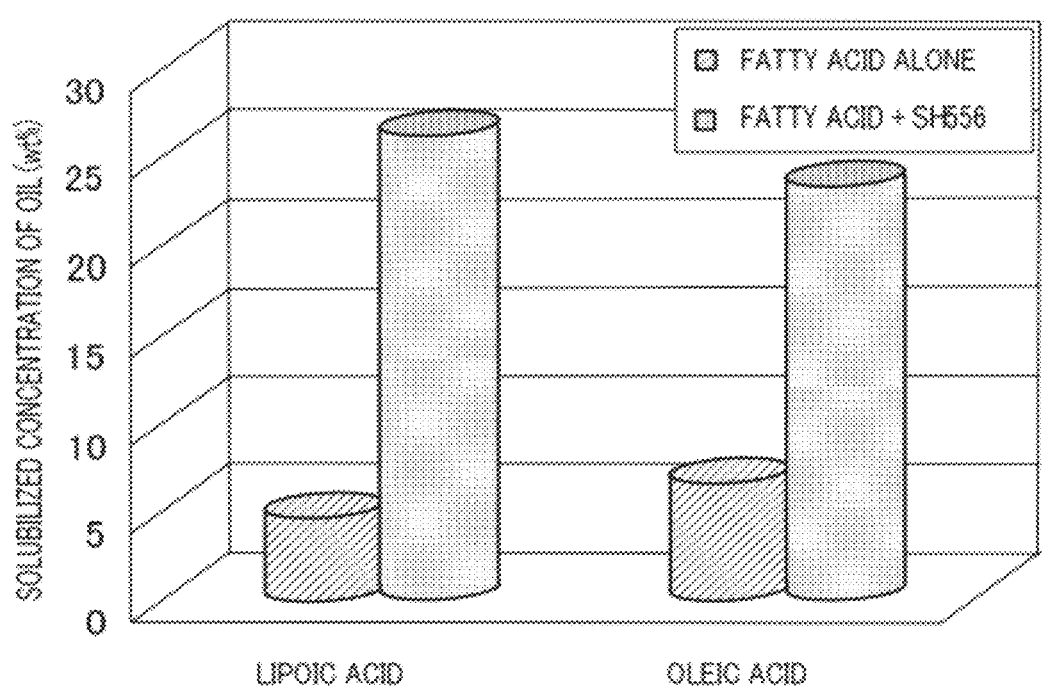
FIG. 10 is a graph showing the solubilized concentration of oil containing a fatty acid when the oil was added to a mixed surfactant aqueous solution.

FIG. 10 is a graph showing the solubilized concentration of oil (a mixed oil of SH556 and α-lipoic acid, a mixed oil of SH556 and oleic acid, α-lipoic acid or oleic acid) when the oil was added to the mixed surfactant aqueous solution. As shown in FIG. 10, the liquid crystal composition of the present invention containing 13.1% by weight of SH556 could contain α-lipoic acid up to 13.1% by weight. Also, the liquid crystal composition of the present invention containing 11.7% by weight of SH556 could contain oleic acid up to 11.7% by weight.

The results described above show that the liquid crystal compositions of the present invention can solubilize fatty acids such as α-lipoic acid and oleic acid.

Example 6

The present example shows that the liquid crystal compositions of the present invention can solubilize ester oils and hydrocarbon oils.

As silicone surfactants, the aforementioned SS-2804 and SS-2910 were prepared. As a phenyl-modified silicone oil, the aforementioned SH556 (monophenyl silicone oil) was prepared. Also, as an ester oil, cetyl isooctanoate (CIO; Kaneda Corporation) was prepared. As a hydrocarbon oil, liquid paraffin (HICALL K-160; Nikko Chemicals Co., Ltd.) was prepared.

In the same procedure as in Example 1, SS-2804, SS-2910 and pure water were mixed until the mixture becomes uniform, thereby preparing an 80% by weight mixed surfactant aqueous solution (transparent liquid crystal composition). Then, a mixed oil of SH556 and cetyl isooctanoate or a mixed oil of SH556 and liquid paraffin was added to the mixed surfactant aqueous solution, thereby preparing the liquid crystal compositions of the present invention. The weight ratio of SH556 and cetyl isooctanoate or liquid paraffin is 1:1 in each mixed oil. Moreover, as comparative examples, cetyl isooctanoate alone or liquid paraffin alone was added to the mixed surfactant aqueous solution to prepare liquid crystal compositions for the comparative examples.

The solubilized concentration of oil (a mixed oil of SH556 and cetyl isooctanoate, a mixed oil of SH556 and liquid paraffin, cetyl isooctanoate or liquid paraffin) in each liquid crystal composition was evaluated. The solubilized concentration (saturated concentration of solubilization) of oil was measured by sample appearance, for example, cloudiness or phase separation.

Figure 11:
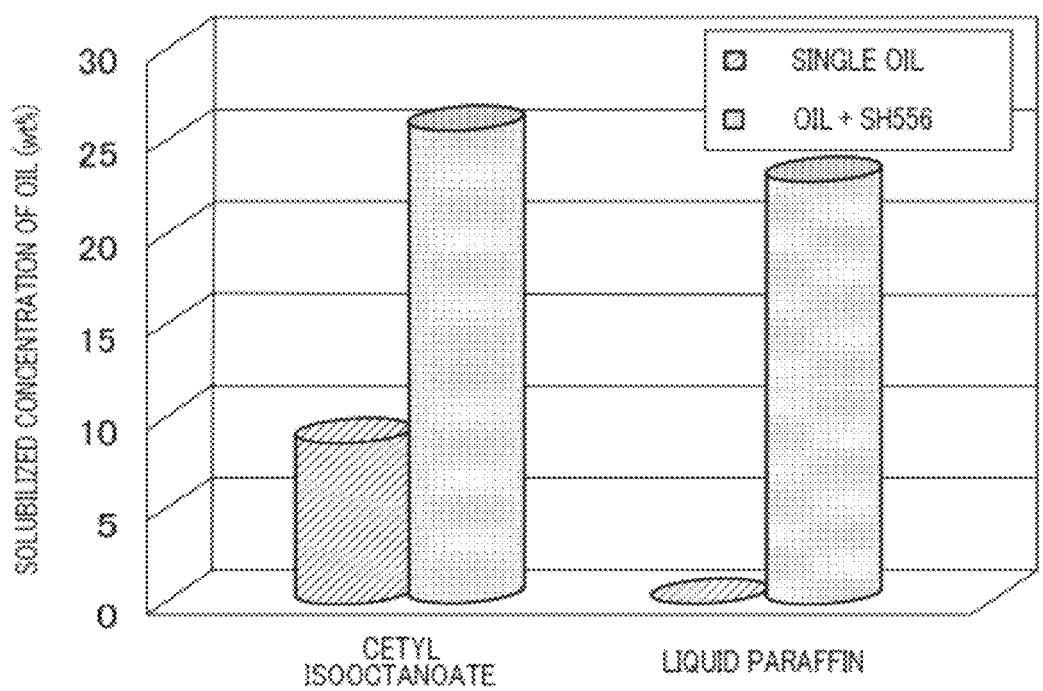
FIG. 11 is a graph showing the solubilized concentration of oil when the oil containing an ester oil or hydrocarbon oil was added to a mixed surfactant aqueous solution.

FIG. 11 is a graph showing the solubilized concentration of oil (a mixed oil of SH556 and cetyl isooctanoate, a mixed oil of SH556 and liquid paraffin, cetyl isooctanoate or liquid paraffin) when the oil was added to the mixed surfactant aqueous solution. As shown in FIG. 11, the liquid crystal composition of the present invention containing 12.96% by weight of SH556 could contain cetyl isooctanoate up to 12.96% by weight. Also, the liquid crystal composition of the present invention containing 11.54% by weight of SH556 could contain liquid paraffin up to 11.54% by weight.

The results described above show that the liquid crystal compositions of the present invention can solubilize ester oils such as cetyl isooctanoate and hydrocarbon oils such as liquid paraffin.

Example 7

The present example shows that among surfactants silicone surfactants are compatible with a phenyl-modified silicone oil.

As surfactants, HCO40 (polyoxyethylene hydrogenated castor oil), AOT (sodium bis(2-ethylhexyl)sulfo-succinate) and EOD (polyoxyethyleneoctyldodexylether) were prepared in addition to the aforementioned SS-2804 and SS-2910. Also, as a phenyl-modified silicone oil, the aforementioned SH556 was prepared.

In the same procedure as in Example 1, surfactant(s) and pure water were mixed until the mixture becomes uniform, thereby preparing an 80% by weight SS-2804/SS-2910 aqueous solution (lamellar liquid crystal), 70% by weight HCO40 aqueous solution (hexagonal liquid crystal), 70% by weight AOT aqueous solution (lamellar liquid crystal) and 80% by weight EOD aqueous solution (lamellar liquid crystal). The weight ratio of two kinds of surfactants is 1:1 in the SS-2804/SS-2910 aqueous solution. Then, SH556 was added to each surfactant aqueous solution to prepare the liquid crystal composition of the present invention and liquid crystal compositions for the comparative examples.

The solubilized concentration of SH556 in each liquid crystal composition was evaluated. The solubilized concentration (saturated concentration of solubilization) of SH556 was measured by sample appearance, for example, cloudiness or phase separation.

Figure 12:
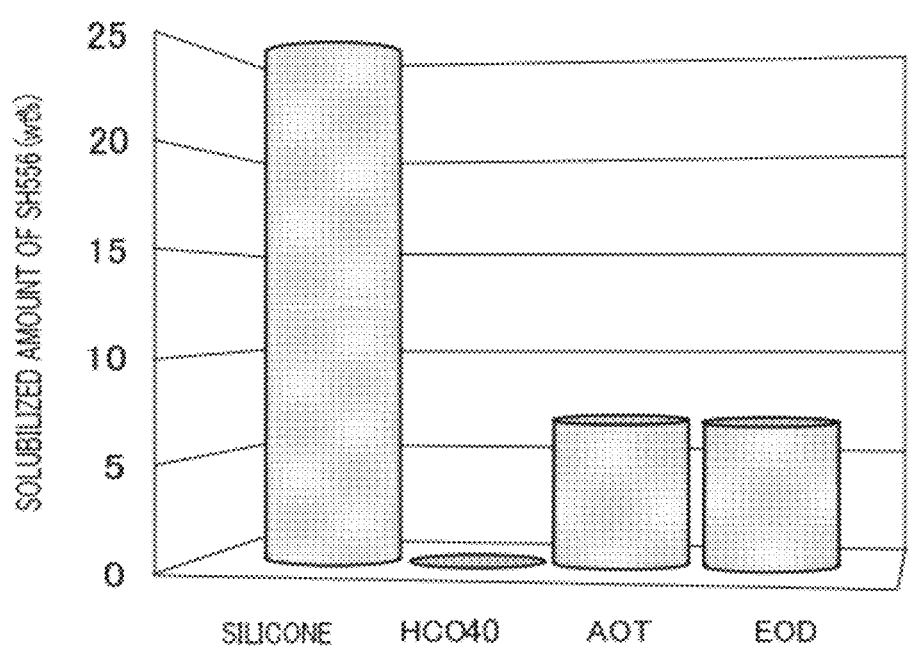
FIG. 12 is a graph showing the solubilized concentration of SH556 when SH556 was added to surfactant aqueous solutions containing silicone surfactants or a hydrocarbon surfactant.

FIG. 12 is a graph showing the solubilized concentration of SH556 when SH556 was added to the surfactant aqueous solutions. As shown in FIG. 12, the liquid crystal composition containing silicone surfactants could contain a larger amount of SH556 than the liquid crystal compositions containing other hydrocarbon surfactants.

The results described above show that among surfactants silicone surfactants are compatible with a phenyl-modified silicone oil.

Reference Example

The present reference example shows that liquid crystals can be formed by using one kind of or two or more kinds of silicone surfactants.

1. Combinations of one kind of silicone surfactant and water Seven kinds of silicone surfactants (polyether-modified silicone (pendant-type), Dow Corning Toray Co., Ltd.) shown in the aforementioned Table 1, one kind of silicone surfactant (polyether-modified silicone (AB-type), Dow Corning Toray Co., Ltd.) shown in Table 3, and 7 kinds of silicone surfactants (polyether-modified silicone (pendant-type), Shin-Etsu Chemical Co., Ltd.) shown in Table 4 were prepared.

TABLE 3

| Product name | Main component | HLB value | Viscosity (mm$^2$/s) |
|---|---|---|---|
| FZ2233 | polysilicon-13 | 2.5 | 5000 |

TABLE 4

| Product name | Main component | HLB value | Viscosity (mm$^2$/s) |
|---|---|---|---|
| KF-6011P | PEG-11 methylether dimethicone | 14.5 | 140 |
| KF-6013 | PEG-9 dimethicone | 10.0 | 400 |
| KF-6015 | PEG-3 dimethicone | 4.5 | 150 |
| KF-6016 | PEG-9 methylether dimethicone | 4.5 | 150 |
| KF-6017P | PEG-10 dimethicone | 4.5 | 850 |
| KF-6028P | PEG-9 polydimethyl siloxyethyl dimethicone | 4.0 | 900 |
| KF-6043 | PEG-10 dimethicone | 14.5 | 400 |

Pure water was added to each silicone surfactant to observe whether or not a liquid crystal structure was formed. The amount of pure water was 10% by weight, 30% by weight, 70% by weight or 99% by weight.

Table 5 is a table showing the relationship between the amount of water and the presence of a liquid crystal structure in the mixtures of one kind of surfactant and pure water.

TABLE 5

| | Amount of pure water | | | |
|---|---|---|---|---|
| Surfactant | 10% by weight | 30% by weight | 70% by weight | 99% by weight |
| SH3772M | ○ | ○ | ● | ● |
| SH3773M | ◎ | ○ | ● | ● |
| SH3775M | ◎ | X | X | ○ |
| SS2802 | Δ | — | Δ | — |

TABLE 5-continued

| Surfactant | Amount of pure water | | | |
|---|---|---|---|---|
| | 10% by weight | 30% by weight | 70% by weight | 99% by weight |
| SS2804 | Δ | Δ | Δ | — |
| SS2910 | ⊙ | X | X | X |
| FZ2233 | ● | ● | ● | — |
| KF-6011P | Δ | Δ | Δ | — |
| KF-6013 | ⊙ | ⊙ | ○ | ● |
| KF-6015 | ● | X | X | X |
| KF-6016 | ● | X | X | X |
| KF-6017P | ⊙ | X | X | X |
| KF-6028P | ○ | X | X | X |
| KF-6043 | Δ | Δ | Δ | — |

⊙: single liquid crystalline phase (single phase)
○: mixed liquid crystalline phase (two or more phases)
●: emulsion
Δ: isotropic solution (micellar solution or monodispersed solution)
X: solid phase + aqueous phase (including a gel state)

Table 5 shows that when one kind of silicone surfactant and water are combined, it is preferable to use a silicone surfactant having a HLB value of 4.0 to 10.0 and a viscosity of 400 mm$^2$/s or more.

2. Combinations of two kinds of silicone surfactants and water Among 7 kinds of silicone surfactants (polyether-modified silicone (pendant-type), Dow Corning Toray Co., Ltd.) shown in Table 1, two kinds of surfactants (the first surfactant and the second surfactant) were mixed to prepare mixtures of silicone surfactants. The amounts of the first surfactant and the second surfactant were both 0.8 g. That is, the mixing ratio of two kinds of surfactants is 1:1 (weight ratio). Pure water was added to the obtained mixtures of silicone surfactants to observe whether or not a liquid crystal structure was formed. The amount of pure water was 10% by weight or 20% by weight.

Table 6 is a table showing the relationship between combinations of two kinds of surfactants and the presence of a liquid crystal structure.

TABLE 6

| Surfactant | | Amount of pure water | |
|---|---|---|---|
| First surfactant | Second surfactant | 10% by weight | 20% by weight |
| SH3771M | SH3772M | ⊙ | ⊙ |
| | SH3773M | ⊙ | ⊙ |
| | SH3775M | ⊙ | ⊙ |
| | SS2802 | Δ | Δ |
| | SS2804 | Δ | Δ |
| | SS2910 | ⊙ | ⊙ |
| SH3772M | SH3773M | ⊙ | ⊙ |
| | SH3775M | ⊙ | ⊙ |
| | SS2802 | ⊙ | ○ |
| | SS2804 | ⊙ | ⊙ |
| | SS2910 | ⊙ | ⊙ |
| SH3773M | SH3775M | ⊙ | ⊙ |
| | SS2802 | ⊙ | ○ |
| | SS2804 | ⊙ | ⊙ |
| | SS2910 | ⊙ | ⊙ |
| SH3775M | SS2802 | ⊙ | ○ |
| | SS2804 | ⊙ | ⊙ |
| | SS2910 | ○ | ○ |
| SS2802 | SS2804 | Δ | Δ |
| | SS2910 | ○ | ⊙ |
| SS2804 | SS2910 | ⊙ | ⊙ |

⊙: single liquid crystalline phase (single phase)
○: mixed liquid crystalline phase (two or more phases)
Δ: isotropic solution (micellar solution or monodispersed solution)

Table 6 shows that when surfactants having a large HLB value are combined, liquid crystals are not formed. On the other hand, when a surfactant having a large HLB value and a surfactant having a small HLB value are combined or when surfactants having a small HLB value are combined, liquid crystals are formed.

As described above, liquid crystals can be formed by combining two or more kinds of silicone surfactants with water.

The present application claims priority based on Japanese Patent Application No. 2009-226918 filed on Sep. 30, 2009. The present specification contains the description of the specification and the drawings of the application, the entire contents of which being incorporated herein by reference.

INDUSTRIAL APPLICABILITY

The liquid crystal composition of the present invention can solubilize hydrophobic compounds having poor solubility in water (for example, hydrocarbon oils such as squalane and fatty acids such as oleic acid and lipoic acid). Therefore, the liquid crystal composition of the present invention is useful, for example, as toiletry materials and cosmetic materials.

The invention claimed is:

1. A liquid crystal composition comprising:
   one silicone surfactant,
   a monophenyl silicone oil, and
   water so that the liquid crystal composition consists of a liquid crystal structure,
   wherein the one silicone surfactant has a HLB value between 4.0 to 10.0 and a viscosity between 400 mm$^2$/s and 850 mm$^2$/s, and
   a concentration of the one silicone surfactant in the liquid crystal composition is in the range of 50 to 95% by weight.

2. The liquid crystal composition according to claim 1, wherein the monophenyl silicone oil has a composition ratio of 0.1 to 90% by weight, and the water has a composition ratio of 0.1 to 90% by weight.

3. The liquid crystal composition according to claim 1, wherein the one silicone surfactant is a pendant-type silicone surfactant.

4. The liquid crystal composition according to claim 1, further comprising a hydrocarbon oil, a fatty acid, an ester oil or a combination thereof.

5. The liquid crystal composition according to claim 1, further comprising squalane.

6. The liquid crystal composition according to claim 1, further comprising cetyl isooctanoate.

7. A liquid crystal composition comprising:
   a first silicone surfactant;
   a second silicone surfactant;
   a monophenyl silicone oil; and
   water so that the liquid crystal composition consists of a liquid crystal structure,
   wherein the first silicone surfactant has a HLB value greater than 8.0 and the second silicone surfactant has a HLB value less than 8.0, and
   a total concentration of the first silicone surfactant and the second silicone surfactant in the liquid crystal composition is in the range of 50 to 95% by weight.

8. The liquid crystal composition according to claim 7, wherein the first silicone surfactant and the second silicone surfactant are pendant-type silicone surfactants.

9. A liquid crystal composition comprising:
   a first silicone surfactant having a HLB value of 13.0 and a viscosity of 390 mm$^2$/s;

a second silicone surfactant having a HLB value of 4.0
and a viscosity of 550 mm²/s;
a monophenyl silicone oil; and
water so that the liquid crystal composition consists of a liquid crystal structure,
wherein a total concentration of the first silicone surfactant and the second silicone surfactant in the liquid crystal composition is in the range of 50 to 95% by weight.

* * * * *